United States Patent [19]
Kaesdorf et al.

[11] Patent Number: 5,365,063
[45] Date of Patent: Nov. 15, 1994

[54] METHOD AND APPARATUS OF QUANTITATIVE NON-RESONANT PHOTOIONIZATION OF NEUTRAL PARTICLES AND THE USE OF SUCH APPARATUS

[75] Inventors: Stefan Kaesdorf; Hartmut Schröder, both of München, Germany

[73] Assignee: Der Wissenschaften E.B. Max-Planck-Gesellschaft Zur Foerderung, Goettingen, Germany

[21] Appl. No.: 80,581

[22] Filed: Jun. 21, 1993

Related U.S. Application Data

[63] Continuation of Ser. No. 790,771, Nov. 12, 1991, abandoned.

[30] Foreign Application Priority Data

Nov. 13, 1990 [DE] Germany .................. 40361152

[51] Int. Cl.$^5$ .................. B01D 59/44; H01J 49/00
[52] U.S. Cl. .................. 250/288; 250/282; 250/423 P
[58] Field of Search .......... 250/282, 287, 288, 423 P

[56] References Cited

U.S. PATENT DOCUMENTS

| | | | |
|---|---|---|---|
| 4,694,167 | 9/1987 | Payne et al. | 250/282 |
| 4,733,073 | 3/1988 | Becker et al. | 250/282 |
| 4,920,264 | 4/1990 | Becker et al. | 250/282 |

FOREIGN PATENT DOCUMENTS

WO85/02907 7/1985 European Pat. Off.

OTHER PUBLICATIONS

"Can nonresonant multiphoton ionization be ultrasensitive?"Becker et al., *J. Optics* vol. 2, No. 9, Sep. 1985, pp. 1433–1443.

Kaesdorf et al. "Duennschichttechnologien '90" (VDI-Verlag) and English–language translation thereof.

Conzemius et al. International Journal of Mass Spectrometry and Ion Processes, 61 (1984) 277≧292.

"Laser–induced plasmas" ed. Radziemski et al. pp. 8–17 (Marcel Dekker 1989).

*Primary Examiner*—Bruce C. Anderson
*Attorney, Agent, or Firm*—Handal & Morofsky

[57] ABSTRACT

A method and an apparatus for non-resonant photoionization of multiple species of neutral particles of a gas in which the neutral particles are ionized in an ionization space by a laser beam having a maximum intensity above the saturation intensity for ionizing neutral particles of multiple desired types. The ions so produced are extracted from the ionization space by an ion-optical system. The ionization of the desired types of neutral particles and/or the extraction of the produced ions are confined by light-optical or ion-optical means to a sharply limited space in which the intensity of the laser beam is above the saturation intensity or is negligibly low with respect to the ionization of neutral particles of interest, so that the number of extracted ions of the ion type of interest does not substantially increase when the laser beam intensity is further increased. The multiple ionized species can be quantitatively determined mass spectrographically in a single step.

19 Claims, 4 Drawing Sheets

METHOD AND APPARATUS OF QUANTITATIVE NON-RESONANT PHOTOIONIZATION OF NEUTRAL PARTICLES AND THE USE OF SUCH APPARATUS

This application is a continuation, of application Ser. No. 07/790,771, filed Nov. 12, 1991.

TECHNICAL FIELD

The present invention relates to a method and an apparatus for the quantitative ionization of neutral particles of a gas by means of a non-resonant laser beam. In this context, the term "gas" includes not only permanent gases but also vapors, sputtering products and the like. The neutral particles may be atoms, molecules as well as dimers and clusters, i.e., agglomerates of two or more atoms etc. The method and apparatus according to the invention are especially significant for analytical processes like SALI (Surface Analysis by Laser Ionization), SIMS (Secondary Ion Mass Spectroscopy) and the like, but they may be used quite generally wherever neutral particles are to be ionized within a designated space and as quantitatively as possible.

BACKGROUND OF THE INVENTION

PCT publication WO85/02907 discloses a method for surface analysis in which the surface to be examined is bombarded by an ion beam and the liberated particles are ionized by non-resonant photoionization by means of a high-intensity laser beam parallel to the surface. The produced ions are analyzed by mass spectroscopy with a time-of-flight mass spectrometer of the type "Reflektron".

Non-resonant (non-selective) ionization by means of high-power lasers makes possible the identification of substances with very high sensitivity, but quantification, i.e., a quantitative analysis, has not heretofore been attainable. The above-cited PCT publication states that a saturation of ionization by non-resonant multi-photon ionization is possible but that is true only to a limited degree as shown by more thorough experiments and the cited publication also clearly suggests the semiquantitative character of the described method.

In practice, exact quantification is not possible with the known non-resonant laser ionization methods because of the complicated ionization processes and the multitude of parameters, some of which depend on laser intensity. The term "quantification" refers to the possibility, for a given minimum laser intensity, of deriving the concentration of a substance (element) within a given spatial region ("test volume") from the corresponding ion intensity (i.e, an ion signal).

SUMMARY OF THE INVENTION

The present invention solves the problem of further developing a method for ionizing multiple species of neutral gas particles by non-resonant laser radiation to guarantee quantitative ionization of neutral particles. In a given spatial volume the laser beam in the has an intensity above the saturation intensity of ionization (saturation regime) of each such multiple species. The ionizing laser can have a beam profile with very steep flanks in the given volume. In a preferred embodiment, the produced ions are aspirated by an ion-optical system whose acceptance region, at least in the direction of propagation of the laser beam, is limited to the region in which the laser beam conforms to the above conditions.

The reason for the sharp lateral limitation of the test volume by using a laser beam with steep lateral intensity ramps to above the saturation intensity is that if, for example, the lateral variation of the laser beam intensity is Gaussian, i.e., follows a bell-shaped curve, which is approximately true for many high-power lasers, then the number of ions produced by the laser radiation increases with increasing beam intensity even if the maximum intensity is higher than the saturation intensity.

When the intensity of the laser radiation is increased, the ion density does not increase further in the region where the intensity is greater than the saturation intensity because all the particles are already ionized. However, in the flanks of the radiation profile, where saturation has not yet been attained, the ion density continues to increase so that no saturation of the ion signal, i.e., no signal plateau, is obtainable.

Because the ionization volume increases with increasing intensity, an absolute determination of the ion density in the test volume is possible only with extremely complex apparatus even if the measurements are taken at a fixed laser intensity which is above the saturation intensity. This will be explained for the case where several types of neutral particles having different ionization action crossections are ionized, with the aid of the definition of an "effective test volume".

The total number $N_i$ of ions of particle type i, which, after ionization, pass through the laser beam of the ion aspiration system can be written as:

$$N_i = n_i \int p_i(x,y,z) A(x,y,z) dx dy dz \qquad (1)$$

where $n_i$ : particle density of the particle type i $p_i(x,y,z)$ : probability that the particle type i will be ionized by the laser beam at location (x,y,z)

$A(x,y,z)$ : probability of acceptance

Integration is performed over the ionization space. A constant particle density in the ionization space was assumed and this condition is readily fulfilled as the ionization space usually has a spatial extent of only a few hundred $\mu m$. The integral has the dimension of volume and will be referred-to hereinafter as the test volume $$V_{ieff} = \int p_i(x,y,z) A(s,y,z) dx dy dz \qquad (2)$$

If the laser beam profile does not have very steep flanks and if these flanks are still within the acceptance region of the ion aspiration system, then $p_i(x,y,z)$ is 100% in the saturation regime of the maximum beam profile. When the intensity is increased, the value of $p_i(x,y,z)$ continues to approach that value even at the edges, i.e., the effective test volume $V_{ieff}$ is enlarged.

The measurement of the absolute concentration $n_i$ of the particle type i is thus reduced to the determination of the associated effective test volume $V_{ieff}$ and the measurement of the value $N_i$ of ions of type i which pass the ion aspiration system:

$$n_i = N_i / V_{ieff} \qquad (3)$$

As the probability of ionization $P_i$ depends on both the laser intensity and the ionization action crossection, the effective test volume $V_{ieff}$ is generally an individual property of the particle of type i and thus cannot be determined even with a calibration substance j of known density $n_j$ and known ionization probability $p_i(x,y,z)$. Therefore, previous methods of post-ionization quantification make it necessary, even in the case of saturation of ionization in the center of the beam profile, to measure the three-dimensional test volume to obtain an absolute determination of ion density and that measurement is technically very difficult.

Conditions are further complicated in that, in many instances, several competing ionization processes with varying intensity dependence produce the same ion type. For example, if the sample surface is metallic, then, e.g., dimers and other metal clusters are emitted during sputtering, in addition to metal atoms and, because of the interaction with the laser beam, atomic ions are produced both by ionization and by fragmentation of the dimers and metal clusters. As ion production via clusters is more efficient than ionization of atoms, the dimers and clusters are ionized before the atoms. If the steepness of the flanks of the laser beam is not great enough, then the cluster ionization will predominate overall even for the highest laser power because, even then, the regions of lower intensity at the flanks can still contribute to ionization.

The above described quantification problem is solved, according to the present method and apparatus, by confining the ion production and yield to a sharply limited spatial region by the use of a laser beam having an intensity profile with very steep flanks and by aspirating or detecting only ions from the spatial region in which the intensity is above the saturation intensity and where the laser beam has a steep-flanked intensity profile and where, especially, the process of direct ionization, which is easier to quantify, predominates. This spatial volume does not expand when the laser intensity increases so that the number of ions produced in dependence on laser intensity reaches a plateau in the saturation regime.

For absolute determinations, the size of the test volume in this case can be found by calibration measurements with a calibration substance, such as a noble gas, e.g., xenon, whose particle density can be measured simply and whose ionization process is driven into saturation. Knowledge of the ionization crossection of the calibration substance is not necessary, however. It is sufficient to obtain a plateau to be able to use the number of measured ions and the normally known ion detection sensitivity of the ion detection device being employed, to determine the volume in question from the particle density, assumed known.

The sharp limitation of the test volume can be obtained by a combination of light-optical and ion-optical means. If the laser beam profile has very steep lateral intensity gradients, then the test volume does not have to be limited in that direction by means of the ion-optical part of the ion aspiration system, i.e., the extent of the ionization volume and the test volume are identical in the lateral direction.

Compared to the known method, namely to limit the test volume solely by use of the ion-optical means of the aspiration system, the present method therefore has the advantage that the steps required for quantification of the ionization do not lead to a reduction of the number of aspirated ions. In this way, the high sensitivity of this method of ionization remains intact. In the direction of the laser beam, the test volume must be limited by ion-optical means if the laser beam does not conform everywhere along its direction of propagation to the above named conditions of intensity and intensity profile.

DESCRIPTION OF THE PREFERRED EMBODIMENTS

The invention will now be described in detail with reference to the drawing.

In what follows, the first description will be of the technical methods that can be used for obtaining a sharply limited test volume. The laser beam profile may be optimized by modification of the laser itself or by external means. The first method includes the use of a so-called "unstable" resonator which leads to an increase of intensity at the edges of the beam profile and insures steep flanks in the emitted laser light. If this beam is focussed with aberration-corrected focussing optics, the beam profile is unchanged, i.e., the bundled laser beam also has the desired characteristics. If the flanks of the emitted laser beam are not sufficiently steep, that may be corrected by diaphragms or masks that block the regions of low intensity and/or by the focussing optics. In that case, it is necessary to use focussing optics that generate aberrations during the bundling of the laser beam and thus modify the beam profile, as will be explained in more detail with reference to FIG. 4.

Figure 1:
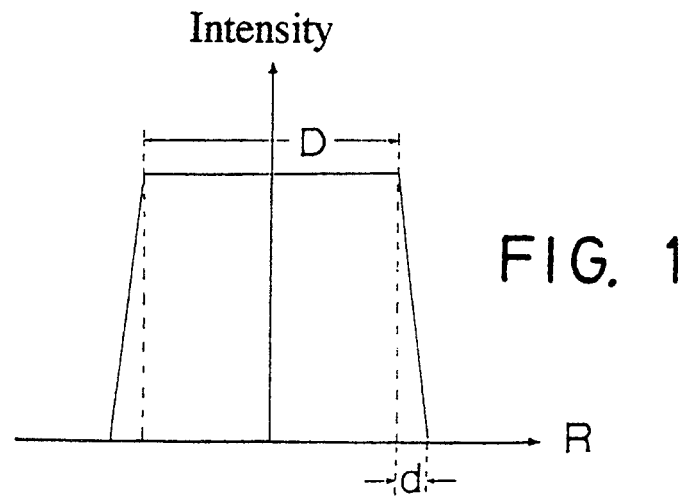
FIG. 1 is a schematic representation of an intensity profile of a laser beam.

The degree of steepness required of flanks of the beam profile depends on the precision with which the absolute ion density in the test volume must be determined. If the ionization crossections of the calibration substance and of the test substance are drastically different, then the largest relative error made during the determination of the absolute ion density in the test volume is given by the ratio of the volume defined by the flanks of the beam profile to the magnitude of the volume, with saturation being always achieved. If a precision G of 10% is required then, for a trapezoidal beam profile with radial symmetry according to FIG. 1, $$G = \pi \cdot D \cdot d/(\pi D^2/4) = 1/10 \text{ or } d < D/40 \quad (4)$$

Figure 2:
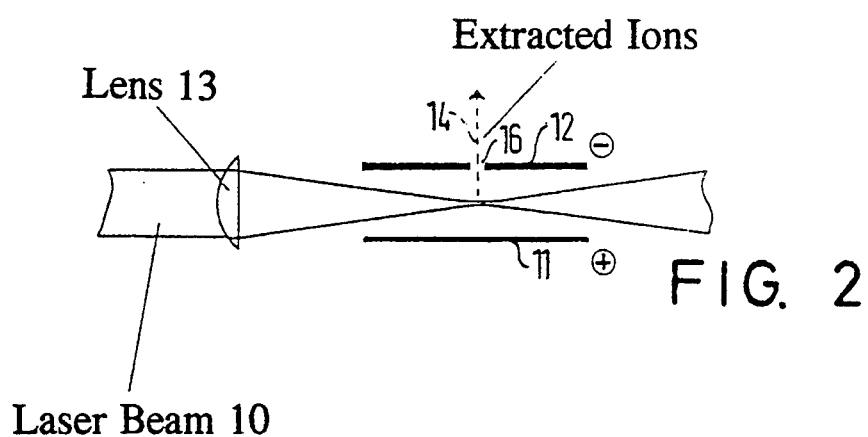
FIG. 2 is schematic representation of a first example of an ion aspiration system.
Figure 3:
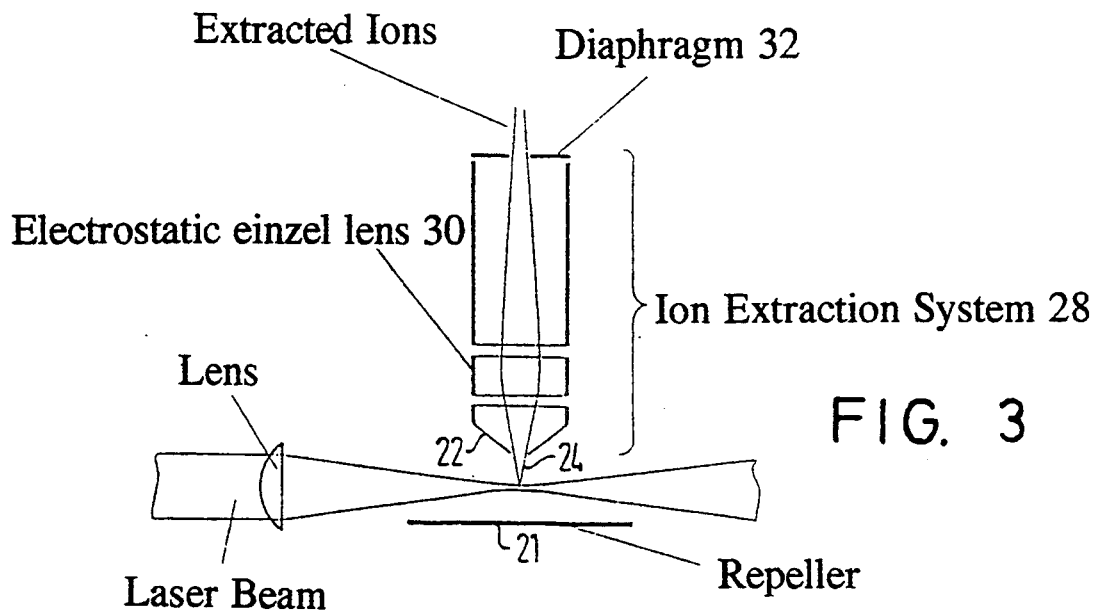
FIG. 3 is a schematic representation of an alternative example of an ion aspiration system.

FIGS. 2 and 3 show means for defining the test volume with the aid of ion-optical devices of the ion aspiration system. In FIG. 2, the ions are produced by a laser beam 10 in a plate capacitor formed, for example, by a flat surface of a probe 11 and by a parallel plane plate 12 and within which exists a homogeneous electric field. The laser beam 10 extends parallel to the electrodes of the plate capacitor 11, 12 and is focussed by a lens 13 into the interior of the plate capacitor. The borders of the test volume in the plane perpendicular to the beam 14 of emerging ions are formed by an opening 16 in the negatively charged plate 12. As the ion-optical construction has unlimited acceptance in the direction of the emerging ion beam, any limitation of the test volume in that direction can occur only by energy selection of the aspirated ions. This energy selection may be performed by an energy spectrometer (e.g., a spherical capacitor type spectrometer of a cylindrical mirror analyzer) mounted behind the drain electrode (plate 12) or, for example, by time-of-flight analysis of the aspirated ions in the case of pulsed ionization.

In the alternative apparatus of FIG. 3, the ions 24 are aspirated by the electric field between a repeller electrode 21 formed, for example, by the probe and an input electrode 22 of an ion extraction system 28 and subsequently imaged ion-optically by a single electrostatic lens 30 on a diaphragm or mask 32. The size of the mask opening thus determines the borders of the test volume. In the direction of the extracted ion beam 24, the test volume is limited by the finite depth of field of the ion-optical image and/or by energy selection. In this case, the lateral ion-optical limitation of the test volume is thus accomplished by diaphragms in the ion-extraction system.

If the laser beam intensity distribution exhibits a structure within the test volume, an increase of laser beam intensity may cause an inward expansion of the test volume which detracts from an exact quantification for the reasons cited above. If the laser beam has a structured intensity distribution, i.e., it exhibits one or more intermediate minima, then the intensity in the minima must be higher than the saturation intensity or, for very steep intensity gradients, either the intensity in the minima must always be negligibly small for all possible intensities of the post-ionization laser beam or else it must always be above the saturation intensity.

Figure 4:
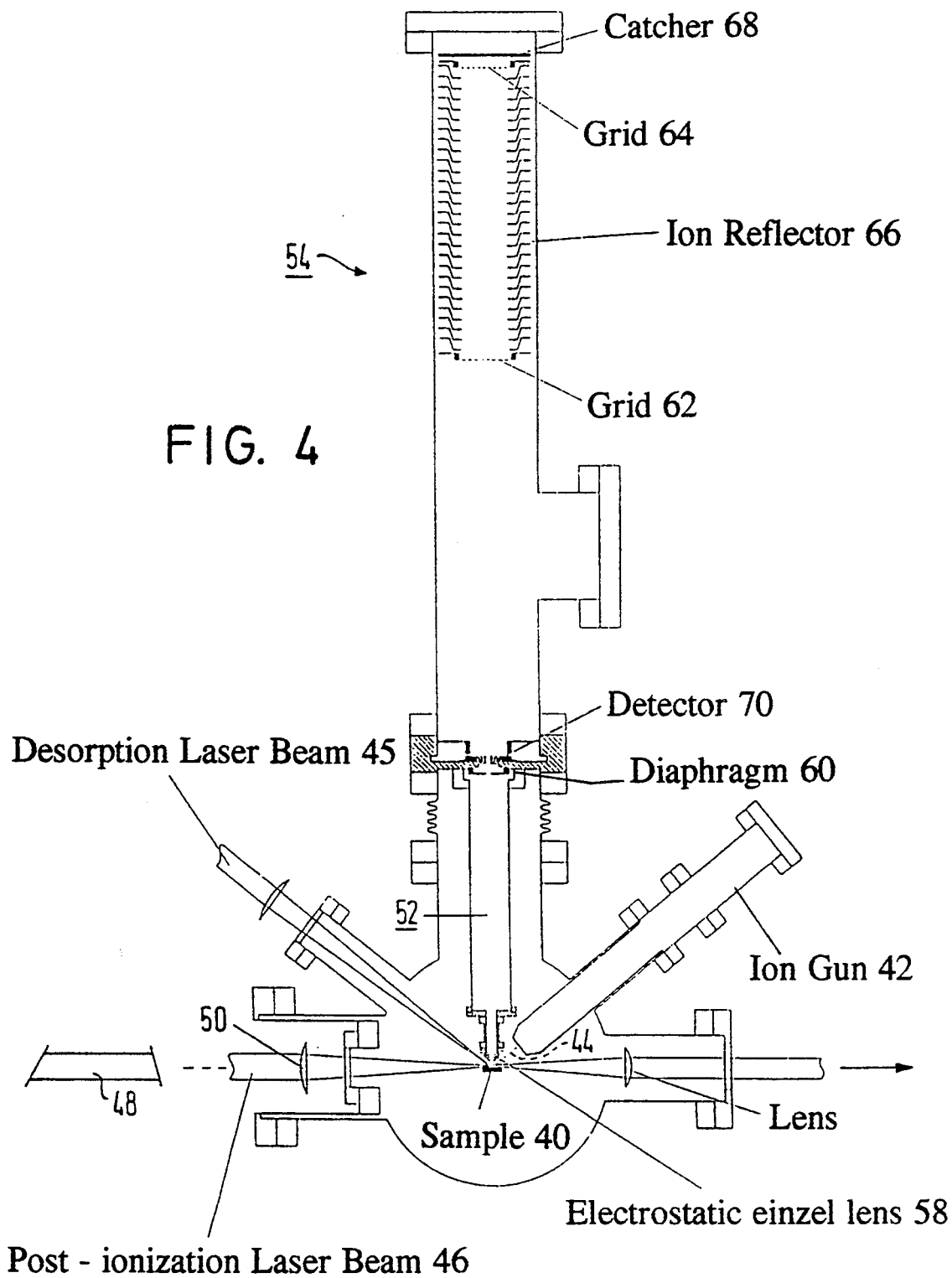
FIG. 4 is an exemplary embodiment of an apparatus for carrying out the method of the invention.

The apparatus shown in FIG. 4, for examining the surface of a probe 40 includes an ion gun 42 for generating an ion beam 44 directed onto the surface of the probe to be analyzed for removing ("sputtering") material from the probe surface. Alternatively, material may be removed from the probe surface by means of a desorption laser beam 45. The neutral component of the sputtered particles is ionized by interaction with a laser beam 46 parallel to the probe surface, produced by a KrF laser 48 shown only schematically and focussed near the probe surface by focussing optics 50 shown for simplicity as a lens. The ions so produced are extracted by an ion extraction module 52 and analyzed in a mass spectrometer 54.

The focussing optics 50 not only bundle the laser beam but also modify its beam profile so that the intensity gradients of the focussed laser beam are as steep as possible within a predetermined volume. The focussing optics 50 may contain or consist of hard and/or soft diaphragms and/or other suitable elements such as lenses. They are so configured that the probe does not enter the laser beam.

Figure 5:
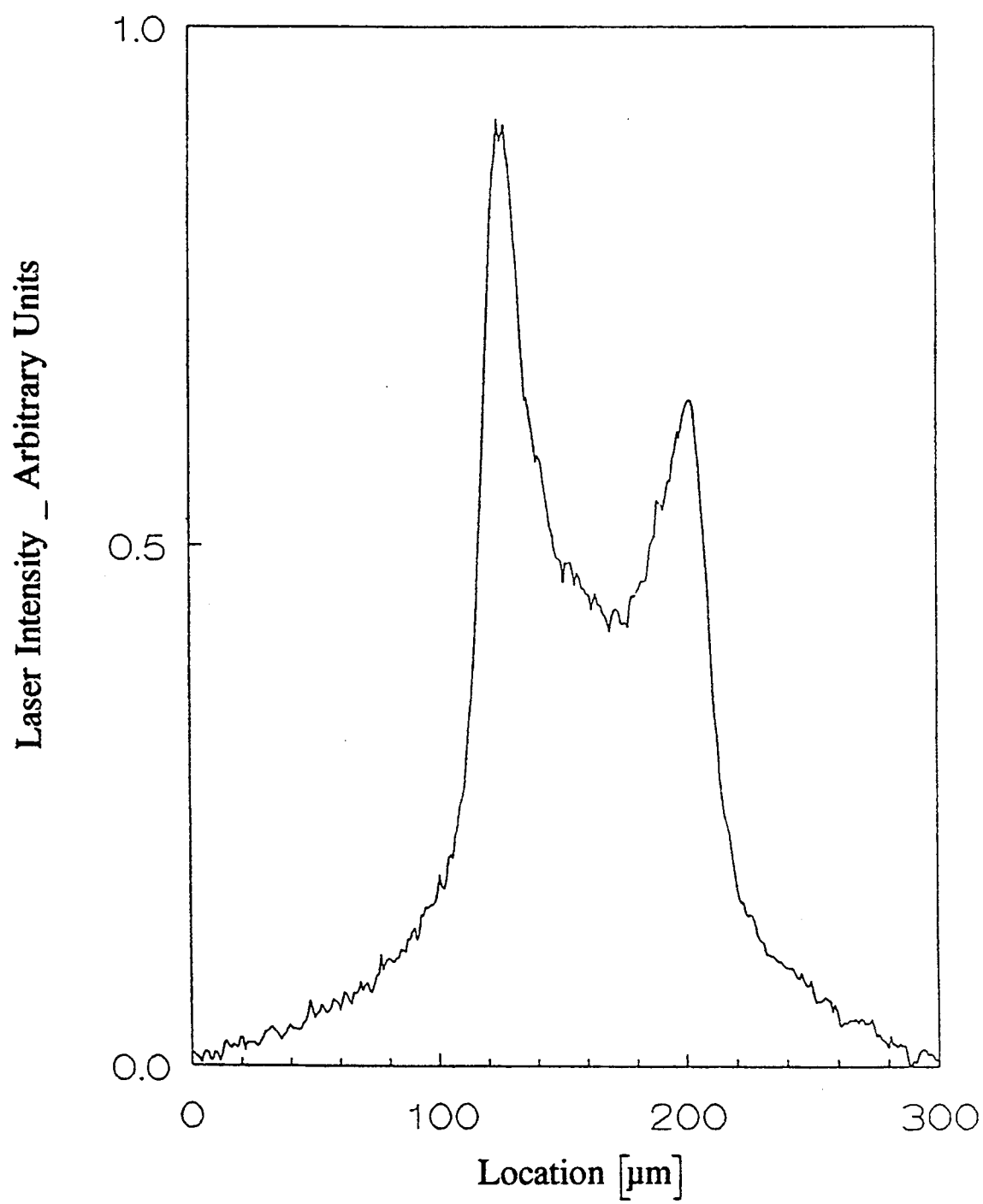
FIG. 5 shows the lateral intensity distribution of a post-ionization laser beam in the ionization chamber and FIG. 6 is a diagram showing the dependence of an ion signal on the intensity of an ionizing laser beam.

A suitable beam profile is shown in FIG. 5. It contains two peaks between which lies a relative intensity minimum. The intensity in the minimum should be above the saturation intensity. The sharp peaks of the intensity profile according to FIG. 5 which create the steep flanks of the beam profile may be produced by the spherical aberration of a plano-convex focussing lens and represent the edge caustic of the focussed laser beam. The limited lateral acceptance of the ion extraction system (FIG. 3) limits the test volume in the direction of propagation of the laser beam to a region ahead of the smallest circle of confusion where the edge caustic occurs and where the intensity is still sufficient.

In a practical embodiment of the apparatus according to FIG. 4, the ion gun delivered an argon ion beam with an energy of 5 kV. The laser 48 was a pulsed KrF excimer laser whose beam 47 was focussed with a plano-convex lens 50 of focal length 180 mm. At its entrance, the ion extraction module contained a single electrostatic lens 58 and the ion-optical limitation of the test volume was obtained as in FIG. 3 by a diaphragm 60. The mass spectrometer was a time-of-flight mass spectrometer of the type 'Reflektron' and contained an ion reflector defined by grids 62, 64, a catcher 68 disposed at the grid 64 and an ion detector 70 disposed at the diaphragm 60.

The ion extraction module was so disposed, relative to the focussing optics 50, that the only ions extracted were those produced within a distance of $1.25+/-0.125$ mm before the smallest circle of confusion, as seen in the direction of propagation of the laser beam 46. The intensity of the laser beam in the test volume was at least $10^{10}$ W/cm$^2$. The dimensions of the test volume transverse to and along, respectively, the direction of propagation were $100 \times 80 \times 250$ μm. The high rate of ionization not only makes possible quantitative measurements but also greatly increases the sensitivity, permitting practically non-destructive surface analysis because only a minute amount of material has to be removed from the surface.

Figure 6:
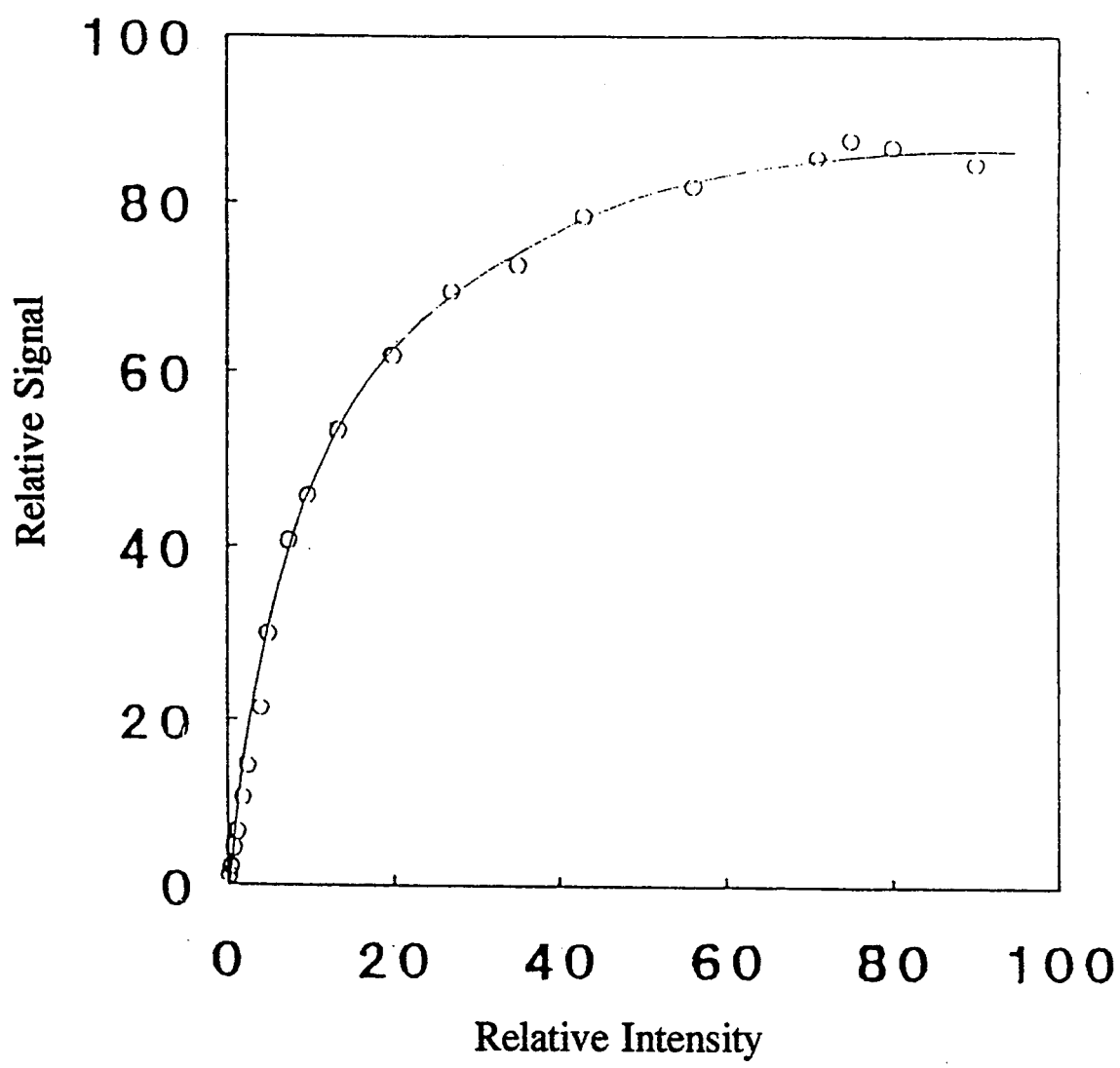

FIG. 6 shows the dependence of the ionization signal on the laser intensity for a copper probe. The measured curve was obtained with the arrangement described above. The occurrence of a saturation plateau at high laser intensities is clearly discernible.

We claim:

1. A method for simultaneous quantitative, non-resonant ionization and quantification of multiple species of neutral particles of a gas, said multiple species of neutral particles each having an ionization saturation intensity said method comprising:
   a) simultaneously ionizing said multiple species of neutral particles to saturation throughout a given spatial volume by means of a laser beam having a direction of propagation toward said spatial volume said beam having an intensity profile across the beam with a high-intensity portion across said spatial volume said high intensity portion exceeding each said saturation intensity of said multiple neutral species whereby each said species is ionized to saturation throughout said given spatial volume; and
   b) extracting said simultaneously ionized particles produced step a) from said spatial volume by means of an ion-optical in extraction system having an acceptance region in said spatial volume; and
   c) simultaneously quantifying said multiple neutral species by mass spectrographic means.

2. A method according to claim 1 further comprising calibration steps of:
   i) introducing a calibration gas of known concentration into said spatial volume; and
   ii) measuring the number of ions produced therein; thereby to determine the magnitude of said spatial volume.

3. A method according to claim 2 further comprising generating said neutral particles by directing an energetic probe beam at a surface in proximity to said spatial volume said probe beam causing said neutral particles to be liberated from said surface.

4. A method according to claim 3 further comprising simultaneously quantifying said multiple ionized species by mass spectrographic means thereby to yield a quantitative analysis of said multiple species at said surface.

5. A method according to claim 2 wherein said plateau intensity of said laser beam is at least $10^{10}$ W/cm$^2$.

6. A method of quantifying neutral species in a gas comprising quantitatively ionizing said neutral species by a method according to claim 1 and simultaneously quantifying said multiple ionized species by mass spectrographic means.

7. A method according to claim 1 wherein said laser beam profile has side portions with a negligible beam intensity and an intermediate portion between said side portions said intermediate portion comprising said high-intensity profile portion.

8. A method according to claim 7 wherein said laser beam profile has steep flanks rising from a level where the ionization probability is negligible to a level above the saturation intensity of each of said multiple species.

9. A method for simultaneous quantitative, non-resonant ionization and quantification of multiple species of neutral particles of a gas, said multiple species of neutral particles each having an ionization saturation intensity said method comprising:
   a) simultaneously ionizing said multiple neutral particles to saturation throughout a given spatial volume by means of a laser beam having a direction of propagation toward said spatial volume and having a beam intensity with a profile having steep flanks, said steep flanks rising from a level at which the ionization probability is negligible to a level above each said saturation intensity of said multiple neutral species said spatial volume being defined between said steep flanks whereby each said species is ionized to saturation throughout said given spatial volume; and
   b) extracting said simultaneously ionized particles produced in step a) from said spatial volume by means of an ion-optical extraction system; and
   c) simultaneously quantifying said multiple neutral species.

10. A method according to claim 9 wherein said ion-optical extraction system has an acceptance region in said direction of laser beam propagation said acceptance region being limited to said high level of said laser beam profile.

11. A method according to claim 9 further comprising calibration steps of:
   i) introducing a calibration gas of known concentration into said spatial volume; and
   ii) measuring the number of ions produced therein; thereby to determine the magnitude of said spatial volume.

12. A method according to claim 9 further comprising generating said neutral particles by directing an energetic probe beam at a surface in proximity to said spatial volume said probe beam causing said neutral particles to be liberated from said surface.

13. A method according to claim 9 wherein said plateau intensity of said laser beam is at least $10^{10}$ W/cm$^2$.

14. A method of quantifying neutral species in a gas comprising quantitatively ionizing said neutral species by a method according to claim 9 and simultaneously quantifying said multiple ionized species by mass spectrographic means.

15. A method according to claim 9 further comprising simultaneously quantifying said multiple ionized species by mass spectrographic means thereby to yield a quantitative analysis of said multiple species at said surface.

16. Apparatus for simultaneous, quantitative, non-resonant ionization and quantification of multiple species of neutral particles of a gas, said multiple species of neutral particles each having an ionization saturation intensity above which ionization does not increase, said apparatus comprising:
   a) laser means to generate a laser beam having a direction of propagation towards a spatial volume to ionize said neutral particles throughout said spatial volume and having a beam intensity profile;
   b) optical focussing means to modify said laser beam intensity profile to have steep flanks each exhibiting a substantial intensity cutoff and having an intensity plateau between said steep flanks said plateau intensity having no significant area beneath any of said multiple species ionization saturation intensities, whereby said multiple neutral species are simultaneously ionized to saturation throughout said spatial volume; and
   c) an ion-optical system for extracting said simultaneously ionized particles from said spatial volume said ion-optical extraction system having an acceptance region in said spatial volume, whereby said ionization is quantitative throughout said spatial volume for each said multiple neutral species; and
   d) means for simultaneously quantifying said multiple neutral species.

17. Apparatus according to claim 16 wherein said optical focussing means comprises an optical device disposed in the path of said laser beam, said optical device having spherical aberration means for focussing the laser beam into a smallest circle of confusion, said spatial volume being disposed before the smallest circle of confusion in the direction of propagation of the laser beam.

18. The use of the apparatus of claim 16 in an analytical instrument.

19. The use of the apparatus of claim 16 in a SALI analytical instrument.

* * * * *

UNITED STATES PATENT AND TRADEMARK OFFICE
CERTIFICATE OF CORRECTION

PATENT NO.  : 5,365,063
DATED       : November 15, 1994
INVENTOR(S) : Kaesdorf

It is certified that error appears in the above-indentified patent and that said Letters Patent is hereby corrected as shown below:

Title page, item [73], Assignee:  should be-- Max-Planck-Gesellschaft Zur Foerderung der Wissenschaften e.V.--

Signed and Sealed this

Ninth Day of May, 1995

Attest:

BRUCE LEHMAN

*Attesting Officer*        *Commissioner of Patents and Trademarks*

UNITED STATES PATENT AND TRADEMARK OFFICE
CERTIFICATE OF CORRECTION

PATENT NO. : 5,365,063
DATED : November 15, 1994
INVENTOR(S) : Kaesdorf

It is certified that error appears in the above-indentified patent and that said Letters Patent is hereby corrected as shown below:

On the title page: Item [73] should read --Max-Planck-Gesellschaft Zur Foerderung Der Wissenchaften E. B. --.

This certificate supercedes the certificate of correction issued May 9, 1995.

Signed and Sealed this

Eighth Day of August, 1995

*Attest:*

BRUCE LEHMAN

*Attesting Officer*     Commissioner of Patents and Trademarks